(12) United States Patent
Schweitzer et al.

(10) Patent No.: US 11,096,575 B2
(45) Date of Patent: Aug. 24, 2021

(54) REBOUND TONOMETER DOCKING STATION AND PROBE DISPENSER

(71) Applicant: Reichert, Inc., Depew, NY (US)

(72) Inventors: James M. Schweitzer, Lancaster, NY (US); Russell J. Bonaventura, Williamsville, NY (US); David A. Taylor, Boston, NY (US)

(73) Assignee: Reichert, Inc., Depew, NY (US)

( * ) Notice: Subject to any disclaimer, the term of this patent is extended or adjusted under 35 U.S.C. 154(b) by 122 days.

(21) Appl. No.: 16/441,067

(22) Filed: Jun. 14, 2019

(65) Prior Publication Data

US 2020/0390331 A1 Dec. 17, 2020

(51) Int. Cl.
*A61B 3/16* (2006.01)

(52) U.S. Cl.
CPC ........ *A61B 3/16* (2013.01); *A61B 2560/0456* (2013.01)

(58) Field of Classification Search
None
See application file for complete search history.

(56) References Cited

U.S. PATENT DOCUMENTS 5,224,594 A * 7/1993 Hou ................. B43M 99/001
206/214
5,772,298 A 6/1998 Miyake 6,623,429 B2 9/2003 Percival et al.
6,849,237 B2 2/2005 Housefield et al.
9,370,296 B2 6/2016 He et al.
2017/0172542 A1 6/2017 Lee et al.

OTHER PUBLICATIONS

ICare Finland Oy, iCare Tonometer Pro User's and Maintenance Manual, Jan. 2012, p. 9, Finland.
ICare Finland Oy, iCare Pro Instruction Manual, 2015, p. 15, Finland.

* cited by examiner

*Primary Examiner* — Matthew Kremer
(74) *Attorney, Agent, or Firm* — Hodgson Russ LLP

(57) ABSTRACT

A docking station for receiving a hand-held rebound tonometer and a probe container carrying disposable tonometer probes has a docking cavity for receiving a portion of the rebound tonometer and a container receptacle for receiving the probe container. The docking station has an actuation feature arranged to move a cover associated with the probe container from a closed position to an open position as the container is inserted into the container receptacle so that tonometer probes in the container are accessible. The actuation feature may include a projection extending into an entryway leading to the container receptacle for engaging the cover but not the container, such that further insertion of the container moves the cover from the closed to the open position. The docking station may also have a storage recess for receiving an empty probe tube and cap after the probe has been removed from the tube for use.

5 Claims, 6 Drawing Sheets

REBOUND TONOMETER DOCKING STATION AND PROBE DISPENSER

FIELD OF THE INVENTION

The present invention relates to contact tonometers of a type utilizing a disposable probe for contacting an eye of a test subject to measure intraocular pressure (IOP).

BACKGROUND OF THE INVENTION

A rebound tonometer is a hand-held instrument that propels a movable measurement probe in a controlled manner toward the cornea of an eye to measure intraocular pressure. During a measurement, the probe contacts the cornea, is decelerated at a rate which depends on intraocular pressure, and then rebounds in a direction away from the cornea back toward the instrument housing. The rebound tonometer detects the motion of the measurement probe and determines intraocular pressure based on the detected motion of the probe. For example, the measurement probe may have a magnetized shaft that travels within a coil in the instrument housing. The coil may be energized momentarily to propel the probe toward the cornea by electromagnetic force, and then, after energizing current to the coil is shut off, a current may be induced in the coil by the moving probe to provide a detectable voltage signal representing velocity of the probe as a function of time. The voltage signal may be recorded and processed to determine a measured IOP value.

For hygienic reasons, the measurement probe which contacts the cornea is a disposable part of the rebound tonometer apparatus. A typical measurement probe comprises a thin metal shaft and a plastic fitting at an end of the shaft having a rounded tip for briefly contacting the cornea without damaging corneal tissue. Commercially available tonometer probes are commonly sold in bulk in a rectangular box container closed by a top cover. Within the container, each individual probe is packaged in a small cylindrical tube closed at one end by a removable cylindrical cap. A typical tube and cap together define a small cylindrical vial about 5 mm in diameter and 45 mm in length.

To use a new probe, the operator must open the cover of the container, withdraw a probe tube from the container, remove the cap from the probe tube, position the probe tube near a measurement head of the rebound tonometer, and tip the probe tube to cause the probe to slide out of the tube such that the shaft of the probe is received into the measurement head of the rebound tonometer.

The procedure for obtaining and installing a new probe has practical drawbacks. Opening the cover on the container can cause jostling and sometimes unintended spilling of probe tubes from the container, especially if the cover snaps open and closed on the container. Once the cover on the container is opened, the container may be inadvertently knocked off a table or other support surface and onto the floor, sending probe tubes in all directions. Because the probe tubes are cylindrical, they have a tendency to roll under furniture and other equipment and often cannot be retrieved. At the same time, the operator may already be holding a selected probe tube removed from the container, making it difficult for the operator to pick up the spilled probe tubes without interrupting the procedure and putting the selected probe tube down on the support surface, where it may get lost. Even if the container is not inadvertently knocked to the ground, the operator must place the empty tube and cap on the table or support surface, or find a waste receptacle in which to throw away the empty tube and cap, after the probe is installed in the rebound tonometer.

SUMMARY OF THE INVENTION

The present disclosure provides a docking station for receiving a hand-held rebound tonometer and a probe container carrying disposable tonometer probes. The docking station generally comprises a support assembly including a base having an upwardly open docking cavity for receiving a portion of the rebound tonometer, and a container receptacle for receiving the probe container. The support assembly is characterized by an actuation feature arranged to move a cover associated with the probe container from a closed position to an open position as the container is inserted into the container receptacle so that tonometer probes in the container are accessible by a user.

In one embodiment, the support assembly may define an entryway into which the container and cover are inserted during insertion of the container into the container receptacle, and the actuation feature may comprise a projection extending into the entryway and arranged to engage the cover but not the container, such that further insertion of the container into the container receptacle causes the cover to move from the closed position to the open position. For example, the actuation feature may comprise an overhanging projection which extends downwardly into the entryway.

The support assembly may further include a storage recess providing a convenient space in which to place an empty cylindrical probe tube and a corresponding cap after the probe itself has been removed from the tube for use in a tonometric measurement.

The docking station of the present disclosure provides a stable home for the probe container to prevent probe spills, and helps keep the work area around the patient well-organized and safe.

BRIEF DESCRIPTION OF THE DRAWING VIEWS

The nature and mode of operation of the present invention will now be more fully described in the following detailed description taken with the accompanying drawing figures, in which.

DETAILED DESCRIPTION OF THE INVENTION

Figure 1:
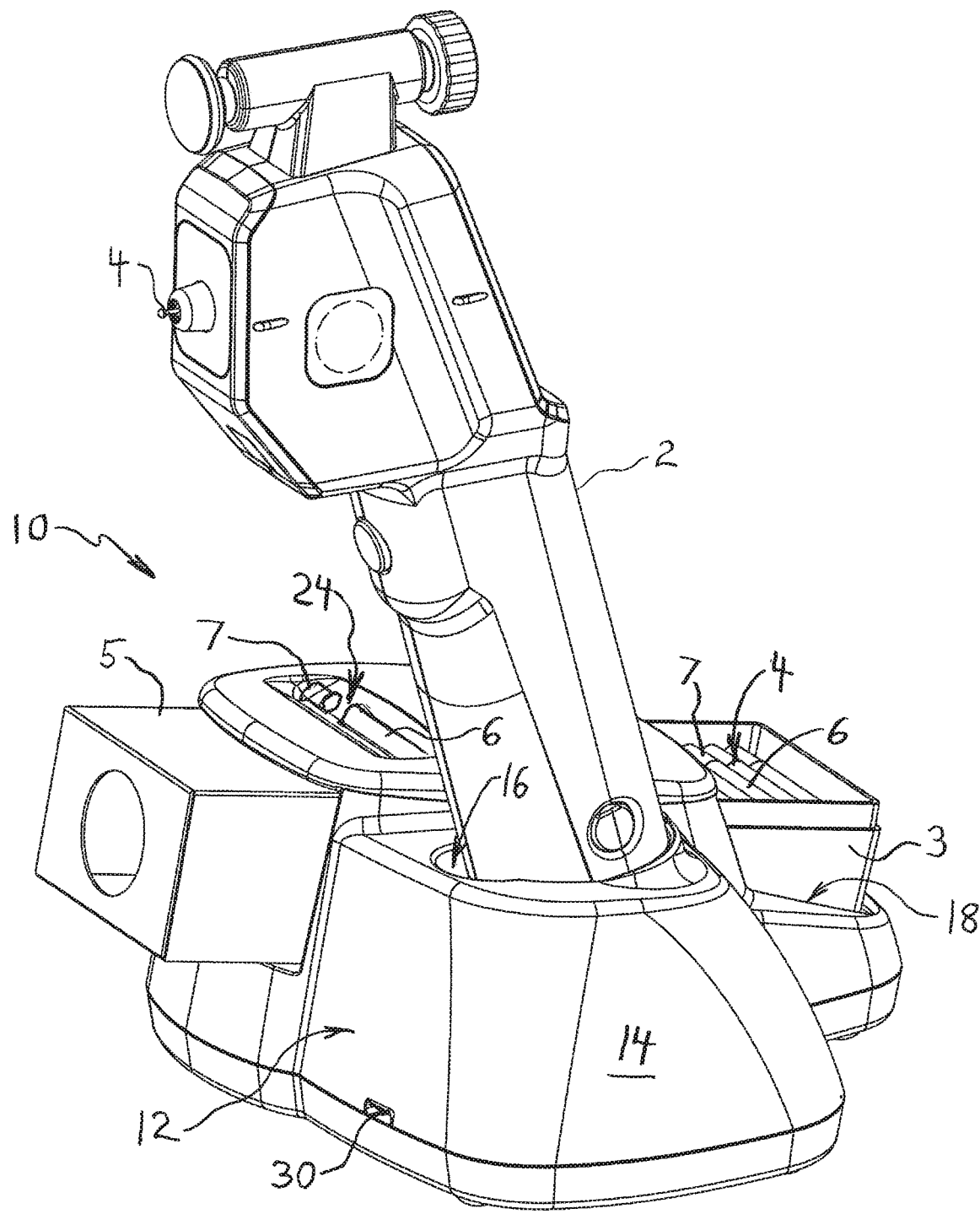
FIG. 1 is a perspective view of a rebound tonometer docking station formed in accordance with an embodiment of the present disclosure, wherein a rebound tonometer and a container of tonometer probes receivable by the docking station are also shown.
Figure 2:
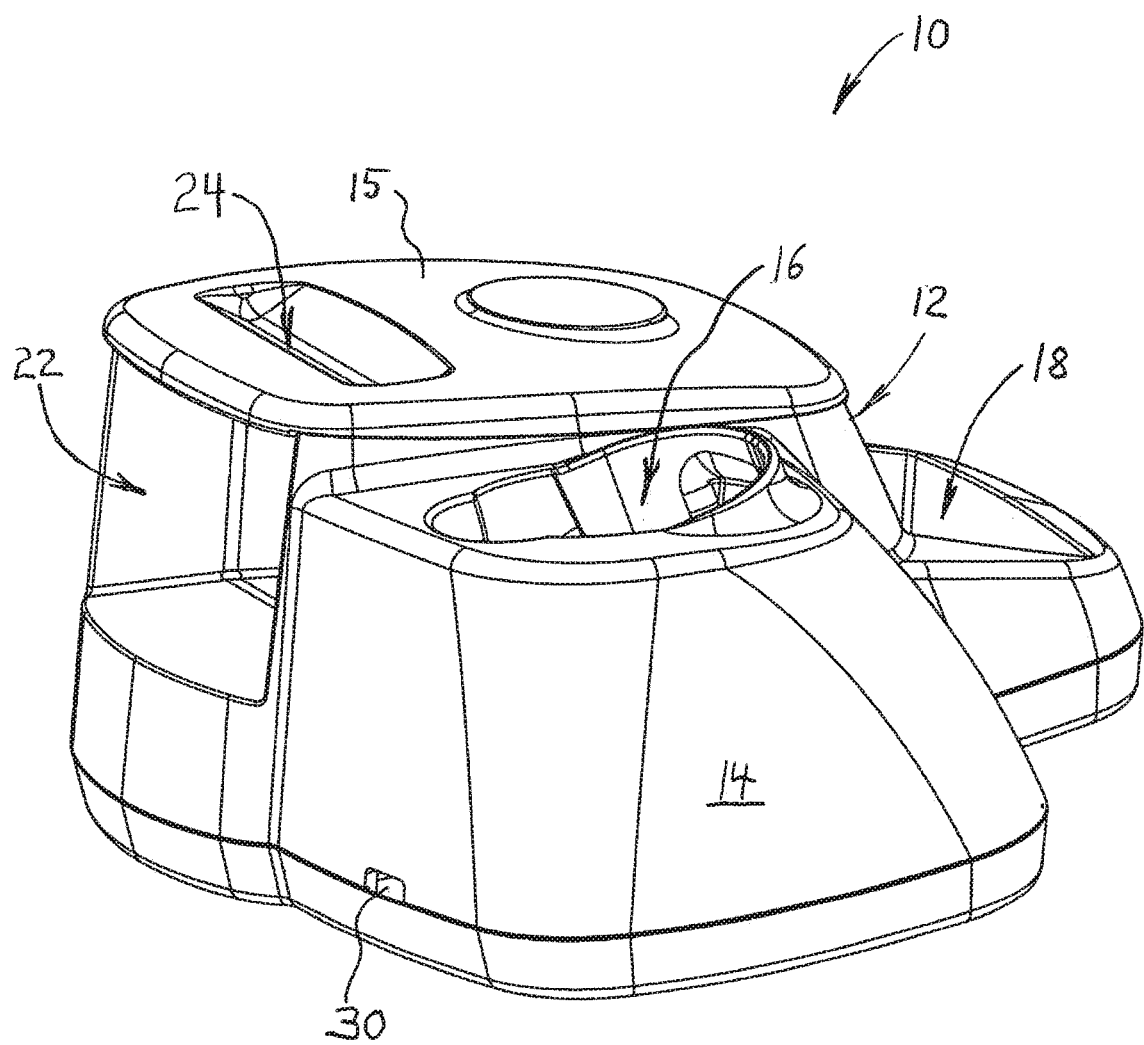
FIG. 2 is another perspective view of the docking station shown in FIG. 1.
Figure 3:
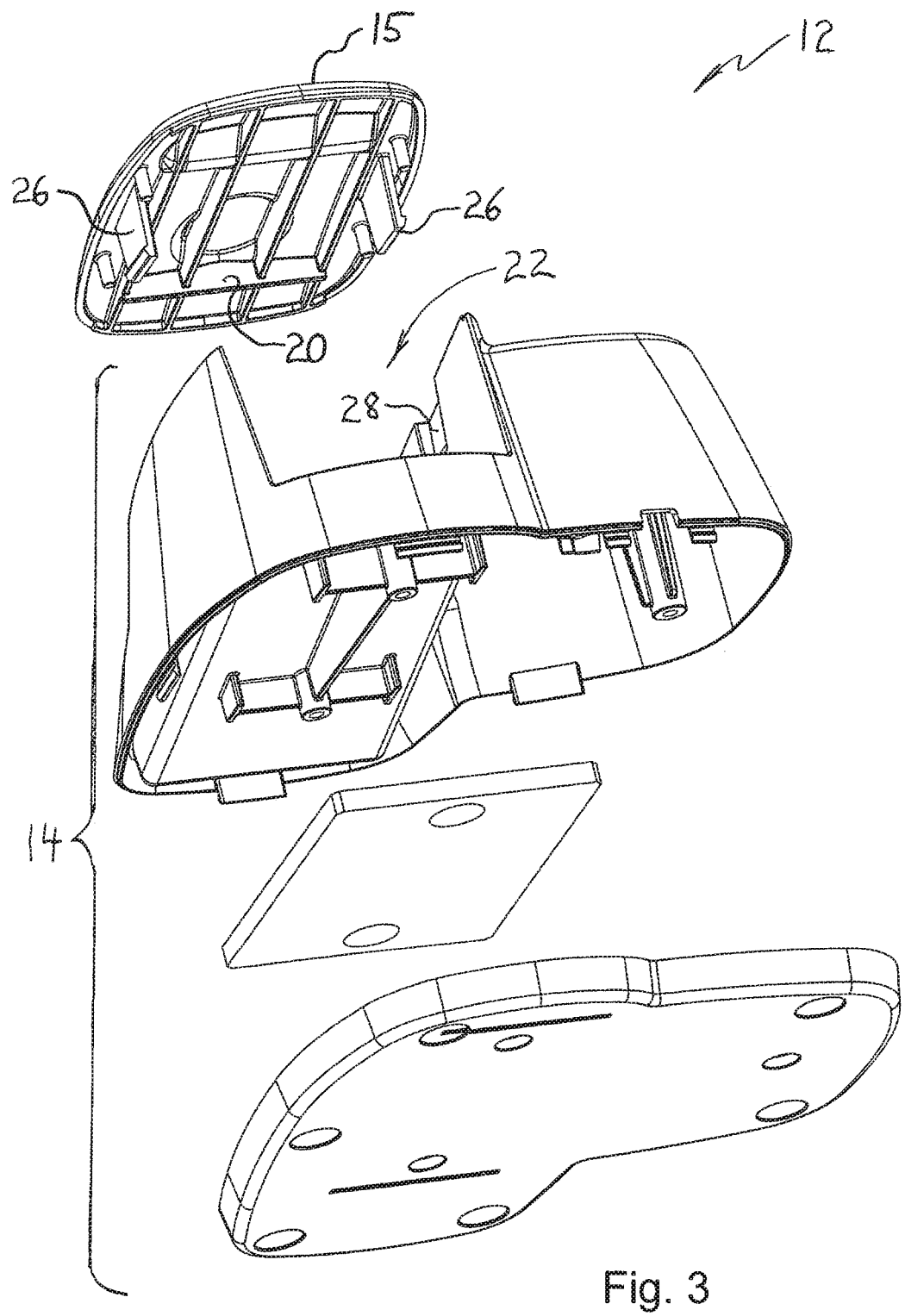
FIG. 3 is an exploded perspective view of the docking station.
Figure 4:
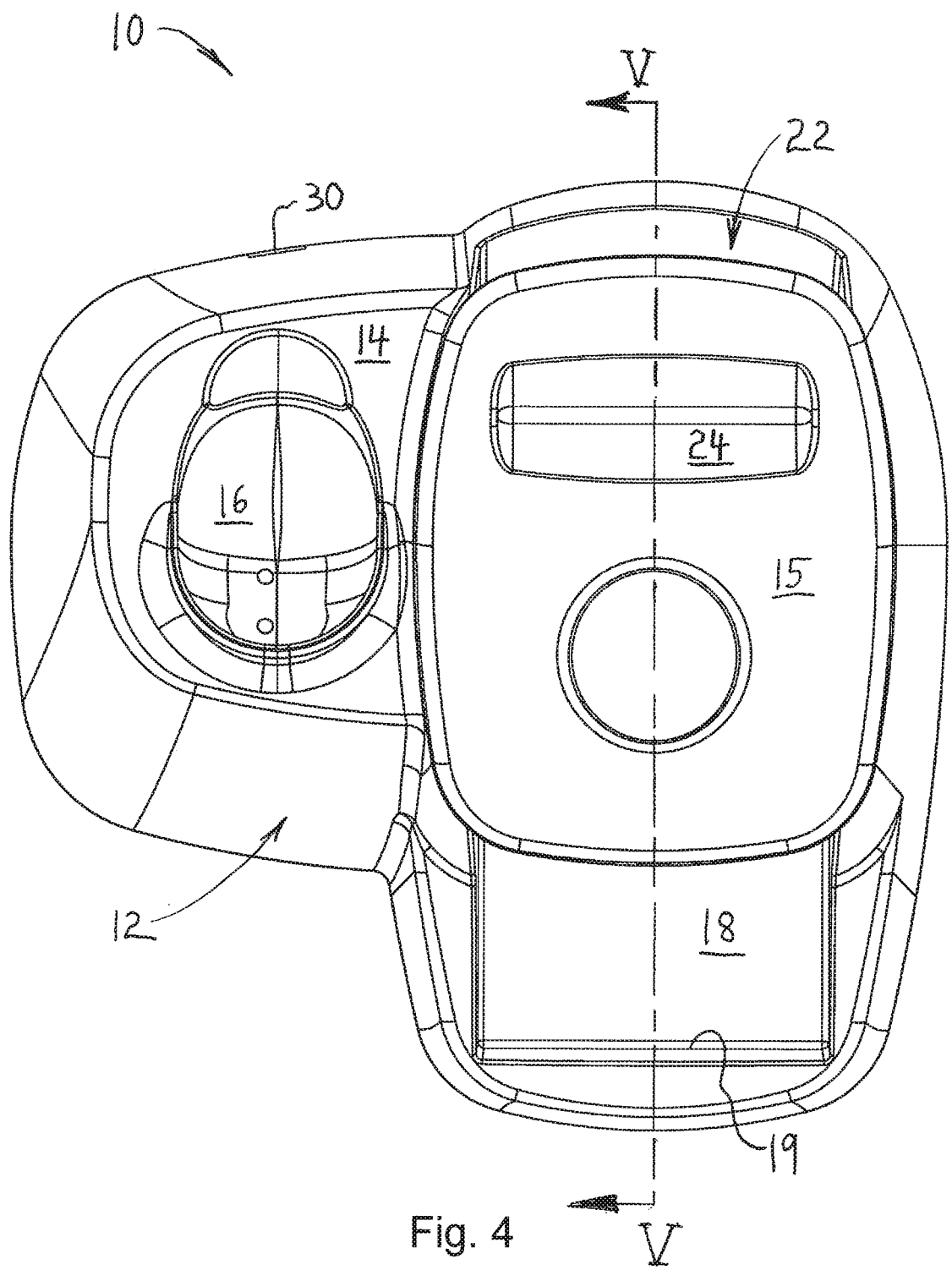
FIG. 4 is a top plan view of the docking station.

FIG. 1 shows a docking station 10 formed in accordance with an embodiment of the present disclosure. Docking station 10 has utility for receiving and supporting a hand-held rebound tonometer 2 and a probe container 3 carrying tonometer probes 4. A cover 5 is associated with container 3 and is movable relative to container 3 from a closed position in which the tonometer probes 4 are confined in the container and an open position in which the tonometer probes 4 are accessible by a user.

Docking station 10 will now be described with reference to FIGS. 2-5 in addition to FIG. 1. Docking station 10 may comprise a support assembly 12 including a base 14 having an upwardly open docking cavity 16 for receiving a portion of rebound tonometer 2, and a container receptacle 18 for receiving probe container 4. Support assembly 12 further includes an actuation feature 20 arranged to move cover 5 from the closed position to the open position as container 3 is inserted into container receptacle 18. As exemplified by the illustrated embodiment, support assembly 12 may include a roof 15 attached to base 14.

Support assembly 12 may define an entryway 22 into which probe container 3 with cover 5 are inserted during insertion of the container into container receptacle 18. Roof 15 may cover at least a portion of entryway 22. Actuation feature 20 may comprise a projection extending into entryway 22 and arranged to engage cover 5 but not container 3. In the illustrated embodiment, actuation feature 20 is an overhanging projection extending downwardly into entryway 22. For example, actuation feature 20 may be an overhanging projection extending downwardly from roof 15. In alternative embodiments, actuation feature 20 may be configured as a lateral projection extending laterally into entryway 22, or as a raised projection extending upwardly into entryway 22.

Figure 5:
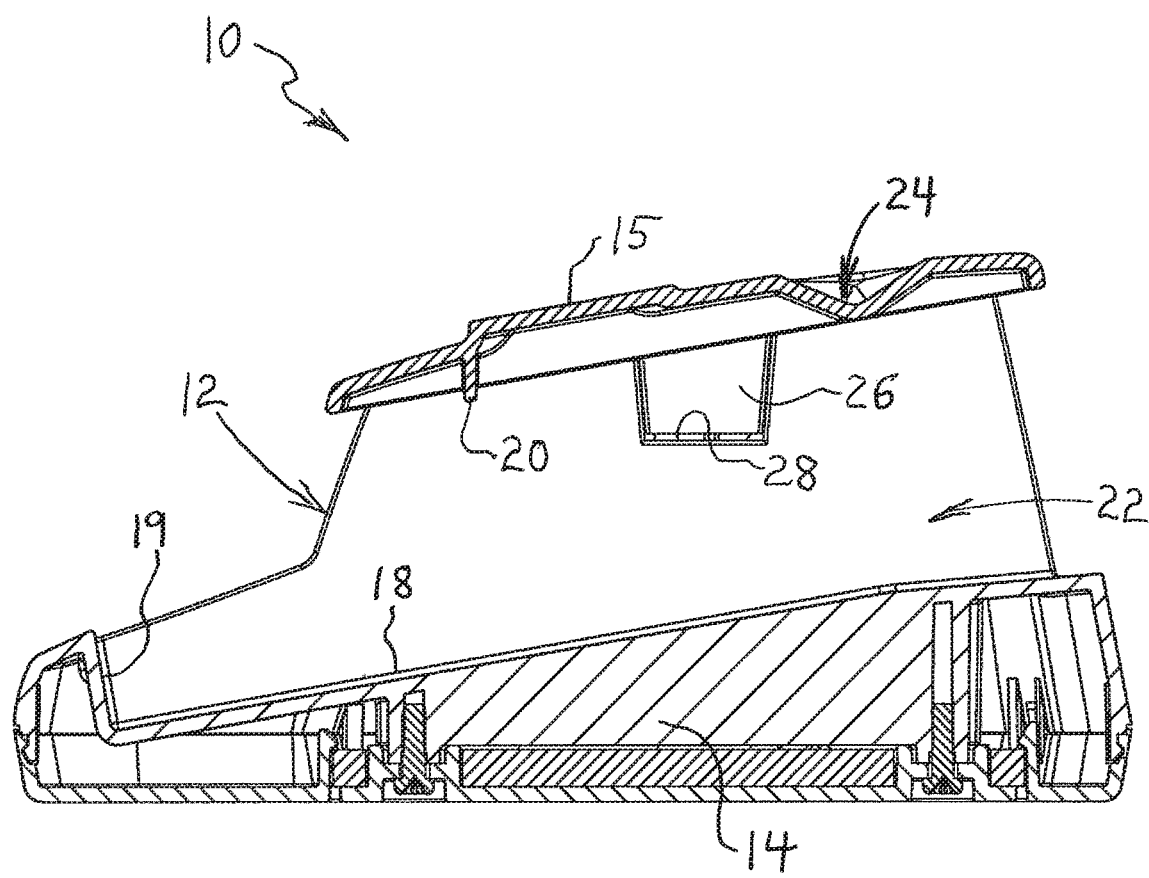
FIG. 5 is a cross-sectional view of the docking station taken generally along the line V-V in FIG. 4.

Container receptacle 18 may be only partially covered by roof 15, such that a user will have easy access to a container 3 received in container receptacle 18. As best seen in FIG. 5, container receptacle 18 may be inclined downwardly in an insertion direction of container 3. Container receptacle 18 may terminate at an end wall 19 against which a leading end of container 3 will abut when container 3 is fully inserted into container receptacle 18.

Support assembly 12 may further include a storage recess 24 sized to receive a cylindrical probe tube 6 and a corresponding cap 7 in which a measurement probe 4 was packaged in sterile fashion prior to use. In the illustrated embodiment, roof 15 includes storage recess 24, however storage recess 24 may be arranged elsewhere on support assembly 12, for example on base 14.

Docking station 10 may serve as a charging station for charging a rechargeable battery (not shown) for powering tonometer 2, and as a data link enabling the tonometer to communicate with an external computer (not shown). For these purposes, docking station 10 may include a USB port 30 electrically connected to the docked tonometer 2. The tonometer battery may be recharged via a USB power adapter plugged into a standard power outlet. Tonometer measurement and usage data may be uploaded from local memory of the tonometer to an external computer having hard drive storage via a USB data cable plugged into a communications port of the external computer. Conversely, software updates may be downloaded from the external computer to the tonometer via the USB data cable.

Base 14 and roof 15 may be molded from plastic. Roof 15 may include resilient attachment members 26 arranged to mate with corresponding niches 28 in base 14 to enable roof 15 to be attached to base 14 in a snap-on manner of assembly.

Reference is now made to FIGS. 6A-6D to describe manual insertion of container 3 into container receptacle 18.

Figure 6A:
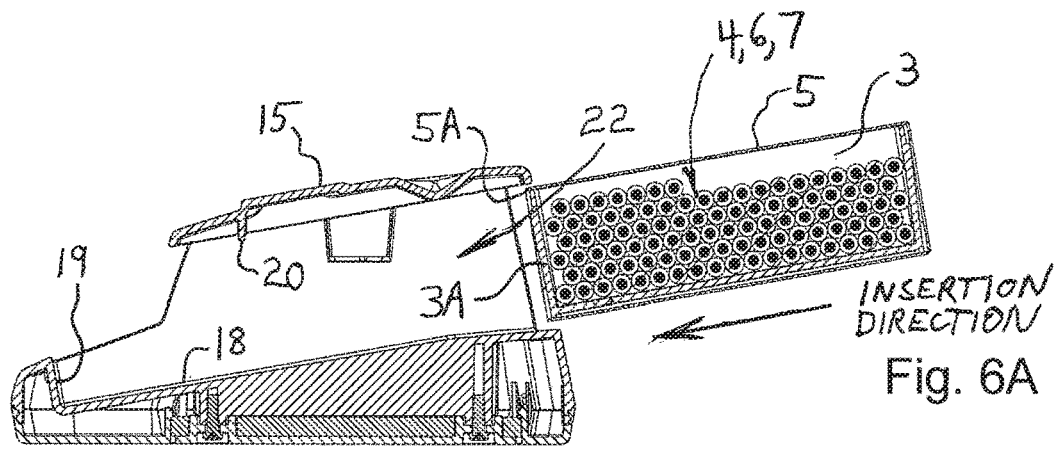
FIGS. 6A-6D are a series of cross-sectional views similar to that of FIG. 5, illustrating insertion of the container of tonometer probes into a container receptacle of the docking station.

As depicted in FIG. 6A, a leading end 3A of container 3 is aligned with entryway 22 in preparation for insertion. As may be seen in FIG. 6A, cover 5 is in the closed position relative to container 3 such that tonometer probes 4 are confined in container 3.

Figure 6B:
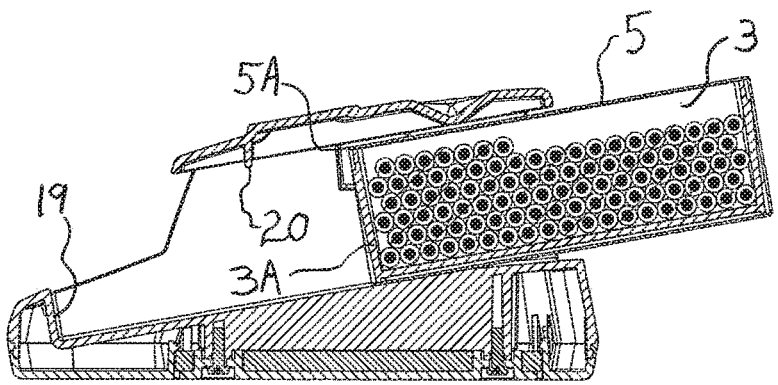

FIG. 6B shows container 3 with cover 5 as container 3 is moved into entryway 22. In FIG. 6B, the leading end 3A of container 3 has not yet reached actuation feature 20, and cover 5 is still in the closed position relative to container 3.

Figure 6C:
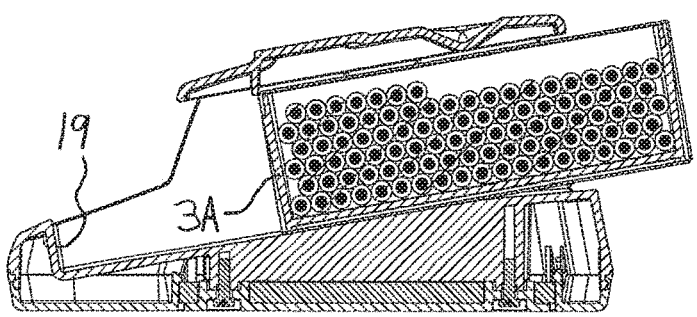

FIG. 6C shows container 3 with cover 5 just as the leading end 3A of container 3 reaches actuation feature 20. In FIG. 6C, cover 5 is still in the closed position, however a leading edge 5A of cover 5 is now engaged by actuation feature 20. Container 3 is not engaged by actuation feature 20.

Figure 6D:
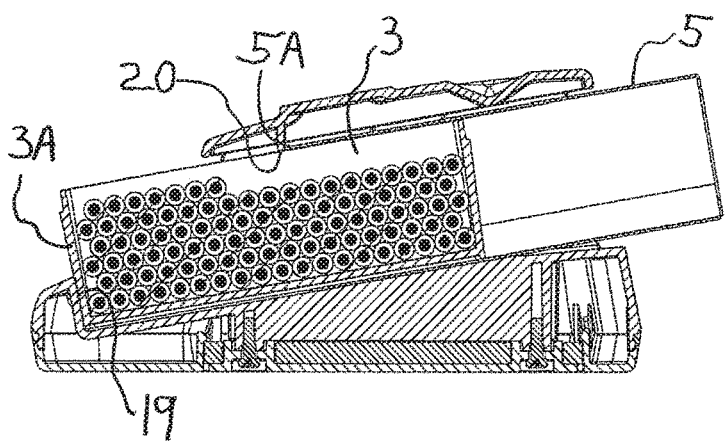

Finally, FIG. 6D shows further insertion of container 3 all the way into container receptacle 18 until leading end 3A abuts with end wall 19. As will be understood, the further insertion of container 3 causes cover 5 to move from the closed position to the open position shown in FIG. 6D, wherein tonometer probes 4 are accessible by a user. In the present embodiment, cover 5 engaged by actuation feature 20 slides telescopically relative to container 3 as the container continues in the insertion direction.

While the present disclosure describes exemplary embodiments, the detailed description is not intended to limit the scope of the appended claims to the particular embodiments set forth. The claims are intended to cover such alternatives, modifications and equivalents of the described embodiments as may be included within the scope of the claims.

What is claimed is:

1. A docking station for receiving a hand-held rebound tonometer and a probe container carrying tonometer probes, wherein a cover is associated with the container and is movable relative to the container from a closed position in which the tonometer probes are confined in the container and an open position in which the tonometer probes are accessible by a user, the docking station comprising:
   a support assembly including a base having an upwardly open docking cavity for receiving a portion of the rebound tonometer and a container receptacle for receiving the probe container, wherein the support assembly defines an entryway into which the container and cover are inserted during insertion of the container into the container receptacle;
   wherein the support assembly further includes a roof attached to the base, wherein the roof covers at least a portion of the entryway; and
   wherein the support assembly further includes a projection extending into the entryway and arranged to engage the cover but not the container to move the cover from the closed position to the open position as the container is inserted into the container receptacle;
   wherein the projection is an overhanging projection extending downwardly into the entryway.

2. The docking station according to claim 1, wherein the overhanging projection extends downward from the roof.

3. The docking station according to claim 1, wherein the container receptacle is partially covered by the roof.

4. The docking station according to claim 1, wherein the container receptacle is inclined downwardly in an insertion direction of the container.

5. The docking station according to claim 1, wherein the roof includes a storage recess.

* * * * *